US006402918B1

(12) United States Patent
Schlenoff et al.

(10) Patent No.: US 6,402,918 B1
(45) Date of Patent: Jun. 11, 2002

(54) APPARATUS FOR CAPILLARY ELECTROPHORESIS AND ASSOCIATED METHOD

(76) Inventors: Joseph B. Schlenoff, 6274 Hines Hill Cir., Tallahassee, FL (US) 32312; Timothy W. Graul, 600 Meridian St. Extension, Apt. 1416, Groton, CT (US) 06340

( * ) Notice: Subject to any disclaimer, the term of this patent is extended or adjusted under 35 U.S.C. 154(b) by 0 days.

(21) Appl. No.: 09/442,198

(22) Filed: Nov. 16, 1999

Related U.S. Application Data
(60) Provisional application No. 60/108,528, filed on Nov. 16, 1998.

(51) Int. Cl.[7] .............................................. G01N 27/453

(52) U.S. Cl. ...................... 204/601; 204/600; 428/34.6; 428/34.7; 428/34.4

(58) Field of Search ................................ 204/601–615, 204/616; 428/34.4, 36.9, 34.7, 36.8

(56) References Cited

U.S. PATENT DOCUMENTS

| | | | | |
|---|---|---|---|---|
| 5,181,999 A | * | 1/1993 | Wiktorowicz | 204/180.1 |
| 5,391,274 A | * | 2/1995 | Shieh | 204/180.1 |
| 5,569,364 A | * | 10/1996 | Hooper et al. | 204/455 |
| 5,716,709 A | | 2/1998 | Ferguson | |
| 6,056,860 A | * | 5/2000 | Amigo et al. | 204/454 |
| 6,074,541 A | * | 6/2000 | Srinivasan | 204/451 |
| 6,117,326 A | * | 9/2000 | Schure et al. | 210/635 |

FOREIGN PATENT DOCUMENTS

| | | | |
|---|---|---|---|
| EP | 0284394 | * | 9/1988 |

OTHER PUBLICATIONS

Ziad El Rassi and Wassim Nashabeh, Capillary Zone Electrophoresis of Biopolymers with Hydrophilic Fused–Silica Capillaries. *Capillary Electrophoresis Technology*, Guzman, N. A. Eds.; Marcel Dekker; New York, 1993 (Chapter 11).

Tarek Farhat, Ghada Yassin, Stephan T. Dubas, and Joseph B. Schlenoff, Water and Ion Pairing in Polyelectrolyte Multilayers 1999 *Langmuir*, vol. 15, No. 20. (pp. 6621–6623).

Mathias Lösche, Johannes Schmitt, Gero Decher, Wim G. Bouwman, and Kristian Kjaer, Detailed Structure of Molecularly Thin Polyelectrolyte Multilayer Films on Solid Substrates as Revealed by Neutron Reflectometry 1998, *Macromolecules*, 31, pp. 8893.

(List continued on next page.)

*Primary Examiner*—Jill Warden
*Assistant Examiner*—Yelena Gakh
(74) *Attorney, Agent, or Firm*—Allen, Dyer, Doppelt, Milbrath & Gilchrist, P.A.

(57) ABSTRACT

An apparatus and method for capillary zone electrophoresis includes a polyelectrolyte multilayer positioned in a capillary tube for analytical separations of macromolecules. The capillary comprises a passage defined by passage walls comprising fused silica. The polyelectrolyte multilayer is positioned within the passage adjacent the walls, and comprises an organic polyelectrolyte. The passage may further comprise nonporous silica particles coated with a multilayer including a plurality of polyelectrolyte layers. An apparatus includes a power supply having a positive electrode and a negative electrode for generating an electric field therebetween. The apparatus includes a capillary having a passage formed by passage walls and comprising therein a polyelectrolyte multilayer positioned substantially within the passage. The passage has a first end electrically connected to the positive electrode and a second end electrically connected to the negative electrode to thereby generate an electric field through the passage. The apparatus also includes a sensor positioned adjacent the passage for sensing macromolecules.

13 Claims, 13 Drawing Sheets

OTHER PUBLICATIONS

Ming Li and Joseph B. Schlenoff, Ion Exchange Using a Scintillating Polymer with a Charged Surface 1994 *Analytical Chemistry*, vol. 66, No. 6, Mar. 15, 1994 (pp. 824–829).

Joseph B. Schlenoff and Ming Li, Kinetics and Multilayering in the Adsorption of Polyelectrolytes to a Charged Surface 1996 *Ber. Bunseges. Phys. Chem,* 100, (pp. 943–947).

Stephan T. Dubas and Joseph B. Schlenoff, Factors Controlling the Growth of Polyelectrolyte Multilayers 1999 *Macromolecules*.

A. A. Morfesis and R.L. Rowell, Microelecrophoresis as a Probe of the Surface Charge of an Expandable–Layer Latex, *Langmuir,* vol. 6, No. 6, 1990 (pp. 1088–1093).

James W. Jorgenson and Krynn DeArman Lukacs, Zone Electrophoresis in Open–Tubular Glass Capillaries, *Analytical Chemistry,* vol. 53, No. 8, Jul. 1981 (pp. 1298–1302).

Yuri Lvov, Katsuhiko Ariga, Izumi Ichinose, and Toyoki Kunitake, Assembly of Multicomponent Protein Films by Means of Electrostatic Layer–by–Layer Adsorption, *J.Am. Chem. Soc.,* vol. 117, No. 22, 1995 (pp. 6117–6123).

Gerald S. Manning, Limiting Laws and Counterion Condensation in Polyelectrolyte Solutions, *The Journal of Chemical Physics,* vol. 51, No. 3, Aug. 1, 1969 (pp. 924–933).

Richard A. Mosher, Chao–Xuan Zhang, Jitka Caslavska, Wolfgang Thormann, Dynamic simulator for capillary electrophoresis with in situ calculation of electroosmosis, *Journal of. Chromatography A,* 716 (1995) (pp. 17–26).

Jonathan S. Green and James W. Jorgenson, Minimizing Adsorption Of Proteins On Fused Silica In Capillary Zone Electrophoresis By The Addition Of Alkali Metal Salts To The Buffers, *Journal of. Chromatography* 478 (1989) (pp. 63–70).

Robert L. Cunico, Victoria Gruhn, Lilia Kresin and Danute E. Nitecki, Characterization of polyethylene glycol modified proteins using charge–reversed capillary electrophoresis, *Journal of Chromatography,* 559 (1991) (pp. 467–477).

Joseph B. Schlenoff, Hiep Ly, and Ming Li, Charge and Mass Balance in Polyelectrolyte Multilayers, *Journal of the American Chemical Society,* 1998, 120 (pp. 7626–7634).

Delphine Laurent and Joseph B. Schlenoff, Multilayer Assemblies of Redox Polyelectrolytes, *Langmuir,* vol. 13, No. 6, 1997 (pp. 1552–1557).

Timothy W. Graul, Ming Li, and Joseph B. Schlenoff, Ion Exchange in Ultrathin Films, *J. of Phys. Chem. B,* vol. 103, No. 14, 1999, (pp. 2718–2723).

Frank Caruso, Edwin Donath, and Helmuth Möhwald, Influence of Polyelectrolyte Multilayer Coatings on Förster Resonance Energy Transfer Between 6–Carboxyfluorescein and Rhodamine B–Labeled Particles in Aqueous Solution, *J. Phys. Chem. B.,* 1998, 102 (pp. 2011–2016).

Ramakrishna S. Madabhushi, Separation of 4–color DNA sequencing extension products in noncovalently coated capillaries using low viscosity polymer solutions, *Electrophoresis,* 1998, 19 (pp. 224–230).

Joel T. Smith and Ziad El Rassi, Capillary zone electrophoresis of biological substances with fused silica capillaries having zero or constant electroosmotic flow, *Electrophoresis* 1993, 14 (pp. 396–406).

Gero Decher, Layered Nanoarchitectures via Directed Assembly of Anionic and Cationic Molecules, *Comprehensive Supramolecular Chemistry,* vol. 9 "Templating, Self–Assembly and Self–Organization" Pergamon Press, Oxford, 1996 J. P. Sauvage and M. W. Hossieini.

Gero Decher, Fuzzy Nanoassemblies: Toward Layered Polymeric Multicomposites, *Science,* vol. 277, Aug. 29, 1997.

G. Decher and J. Schmitt, Fine–Tuning of the film thickness of ultrathin multilayer films composed of consecutively alternating layers of anionic and cationic polyelectrolytes, *Progress in Colloid & Polymer Science,* vol. 89, 1992 (pp. 160–164).

E. Donath, D. Walther, V.N. Shilov, E. Knippel, A. Budde, K. Lowack, C.A. Helm and H. Möhwald, Nonlinear Hairy Layer Theory of Electrophoretic Fingerprinting Applied to Consecutive Layer by Layer Polyelectrolyte Adsorption onto Charged Polystyrene Latex Particles, *Langmuir,* 1997, 13 (pp. 5294–5305).

K. Lowack and C.A. Helm, Molecular Mechanisms Controlling the Self–Assembly Process of Polyelectrolyte Multilayers, *Macromolecules* 1998, 31 (pp. 823–833).

John K. Towns and Fred E. Regnier, Polyethyleneimine–bonded phases in the separation of proteins by capillary electrophoresis, *Journal of Chromatography,* 516 (1990) (pp. 69–78.

Costas Stathakis and Richard M. Cassidy, Cationic Polymers for Selectivity Control in the Capillary Electrophoretic Separation of Inorganic Anions, *Analytical Chemistry,* vol. 66, No. 13, Jul. 1, 1994 (pp. 2110–2115).

John E. Wiktorowicz and Joel C. Colburn, Separation of cationic proteins via charge reversal in capillary electrophoresis, *Electrophoresis,* 1990, 11. 769–773.

Peng Sun, Adam Landman and Richard A. Hartwick, Chitosan Coated Capillary with Reversed Electroosmotic Flow in Capillary Electrophoresis for the Separation of Basic Drugs and Proteins, *J. Microcolumn Separations,* vol. 6, No. 4, 1994, (pp. 403–407).

Qicai Liu and Fangming Lin, Poly(diallyldimethylammonium chloride) as a Cationic Coating for Capillary Electrophoresis, *Journal of Chromatographic Science,* vol. 36, Mar. 1997. (pp. 126–130).

John K. Towns and Fred E. Regnier, Impact of Polycation Adsorption on Efficiency and Electroosmotically Driven Transport in Capillary Electrophoresis, *Analytical Chemistry,* vol. 64, No. 21, Nov. 1, 1992. (pp. 2473–2478).

Web page for Glass Microchannel Plates, dated Nov. 3, 1999. Page operated by the University of California for the U.S. Department of Energy.

Nobuhiko Iki, Edwards S. Yeung, Non–bonded poly(ethylene oxide) polymer–coated column for protein separation by capillary electrophoresis, *Journal of Chromatography A,* 731 (1996) 273–282.

Rick W. Chiu, Juan C. Jimenez, Curtis A. Monnig, High molecular weight polyarginine as a capillary coating for separation of cationic proteins by capillary electrophoresis, *Analytica Chimica Acta,* 307 (1995) 193–201.

O. V. Krokhim, H. Hoshino, O.A. Shpigun, T. Yotsuyanagi, Use of cationic polymers for the simultaneous determination of inorganic anions and metal–4–(2–pyridylazo) resorcinolato chelates in kinetic differentiation–mode capillary electrophoresis, *Journal of Chromatography A,* 776 (1997) 329–336.

Nava Cohen and Eli Grushka, Capillary electrophoresis of proteins using poly–dimethyldiallylammonium chloride as a buffer additive, *J.Cap.Elec.*, 001:2 1994.

Michelle M. Bushey and James W. Jorgenson, Capillary Electrophoresis of Proteins In Buffers Containing High Concentrations Of Zwitterionic Salts, *Journal of Chromatography*, 480 (1989) 301–310.

Kong–Joo Lee and Gwi Suk Heo, Free solution capillary electrophoresis of proteins using untreated fused–silica capillaries, *Journal of Chromatography*, 559 (1991) 317–324.

Randy M. McCormick, Capillary Zone Electrophoretic Separation of Peptides and Proteins Using Low pH Buffers in Modified Silica Capillaries, *Analytical Chemistry*, vol. 60, No. 21, Nov. 1, 1988.2322–2328.

Qicai Liu, Fangming Lin, Richard A. Hartwick, Free Solution Capillary Electrophoretic Separation Of Basic Proteins And Drugs Using Cationic Polymer Coated Capillaries, *J. Liq. Chrom. & Rel. Technol.*, 20(5), 707–718 (1997).

Margrét Thorsteinsdóttir, Roland Isaksson, Douglas Westerlund, Performance of amino–silylated fused–silica capillaries for the separation of enkephalin–related peptides by capillary zone electrophoresis and micellar electrokinetic chromatography, *Electrophoresis* 1995, 16, 557–563.

Kelly A. Cobb, Vladislav Dolnik, and Milso Novotny, Electrophoretic Separations of Proteins in Capillaries with Hhydrolytically Stable Surface Structures, *Analytical Chemistry*, vol. 62, No. 22, Nov. 15, 1990, 2478–2483.

Henk H. Lauer and Douglass McManigill, Capillary Zone Electrophoresis of Proteins in Untreated Fused Silica Tubling, *Analytical Chemistry*, vol. 58, No. 1, Jan. 1986, 166–170.

Danilo Corradini, Buffer additives other than the surfactant sodium dodecyl sulfate for protein separations by capillary electrophoresis, *Journal of Chromatography B*, 699, (1997) 221–256.

Katayama et al. "Stable cationic capillary coating with successive multiple ionic polymer layers for capillary electrophoresis", Anal. Chem., 1998, v. 70, pp. 5272–5277.*

Zhao et al. Anal. Chem., 1993, 65, 2747–2752.*

* cited by examiner

APPARATUS FOR CAPILLARY ELECTROPHORESIS AND ASSOCIATED METHOD

This application is a continuation-in-part of Provisional Application No. 60/108,528, which was filed on Nov. 16, 1998, a date to which priority is claimed under 35 U.S.C. §120 and 37 CFR §1.78, and which Provisional Application is incorporated by reference herein in its entirety.

The claimed invention was made with financial support from the United States Government and the inventors hereby acknowledge that the government may have certain rights in the invention, as specified by law.

FIELD OF THE INVENTION

The present invention relates to the field of molecular separations and, more particularly, to molecular separation by electrophoresis with a polyelectrolyte multilayer positioned. within a very small passage such as in a capillary tube.

BACKGROUND OF THE INVENTION

Electrophoresis is a method for separation of individual molecular species from a mixture by the application of an electric field. The technique relies on the migration of charged molecules through a solution in the electric field. Separation of the molecules occurs due to their different rates of movement through the solution, the rate being influenced by factors such as the pH of the solution, the mass and charge of the molecule, and the strength and duration of the electric field.

The electrophoretic separation may be carried out in a support medium wherein the molecules to be separated are loaded. Common support media for electrophoretic molecular separation include gels of various chemical formulations and physical configurations. Support gels, however, may be difficult to prepare, handle, and process, thereby resulting in reproducibility problems.

One approach for increasing reproducibility has been the use of capillary tubes, but without a support medium for the separation, other than the electrophoresis buffer itself. A capillary tube for use in this technique is substantially a small tube having a void space in the form of a very narrow passage therein. The electrophoretic separation is carried out within the narrow passage. For example, in the late fifties Hjerten reported success in electrophoretic molecular separations using a quartz capillary tube having an internal diameter of about 1–3 mm and using only a suspending solution as the separation medium. Hjerten, *S., Arkivkem,* 1958, 13, 151. Hjerten's system was never commercialized due to problems related to complex design and insufficient heat dissipation during the process. Over the succeeding years other authors reported improved separations and increased heat dissipation using thinner capillaries. In addition, what may be considered the first apparatus for capillary zone electrophoresis was described by Jorgenson and Lukacs. See Jorgenson, J, and K. D. Lukacs, *Anal. Chem.,* 1981, 53, 1298; and *Science,* 1983, 222, 266.

As known in the prior art, capillary zone electrophoresis (CZE) is generally performed as follows. An apparatus for CZE preferably includes a power supply which may provide for reversing polarity, the power supply being connected by each of two electrodes to each of two buffer reservoirs. A fused silica capillary is positioned so as to form a connecting bridge between the two reservoirs. The capillary is generally from about 20 cm to 1 m long, and includes a passage of from about 25 to 100 μm internal diameter. The capillary generally has an outer layer of polyimide to provide added flexibility, as well as durability. Detection of molecular species is performed in an area, or window, of the capillary where the polyimide coating has been stripped away. Suitable detection methods include absorbance, laser-induced fluorescence, refractive index conductivity, electrochemical detection, and even mass spectrometry, although this last approach requires an interface other than the capillary tube.

A sample containing the molecular species to be separated may generally be introduced in the capillary either hydrodynamically or electrokinetically. Those skilled in the art will know that hydrodynamic injection of the sample may be variously accomplished. The capillary may be elevated at one end to inject the sample by substantially syphoning it into the passage. A sample vial may be positioned in fluid connection with the passage, and fluid pressure may be applied to the capillary or to the sample vial to thereby move the sample into the passage. Conversely, suction may be applied at a second end of the passage to draw sample from a sample vial connected to a first end of the capillary. Injection may also be accomplished by means of a syringe, and may preferably include a sample splitter. Electrokinetic injection relies on the application of an initial voltage through the passage to initiate sufficient fluid flow to bring the sample into the passage, thereafter initiating predetermined electrophoretic separation conditions.

Commercially available systems for CZE also include features for rinsing, and for added heat dissipation. Rinsing is accomplished by flushing a rinse fluid through the passage, the rinse fluid usually being water, a buffer, or another predetermined solution. Rinse cycles may be effected by applying pressure to the system to thereby flush the rinse fluid through the microchannel. For added heat dissipation, commercial systems include a coolant feature. For example a fluorocarbon fluid may be used to bathe the capillary so as to prevent uneven heat dissipation during the electrophoresis.

Molecular separation by electrophoresis relies on the electrical interactions affecting the molecular species being separated. The passage walls defining the passage have naturally occurring electrical charges on their surfaces. In a fused silica capillary, for example, surface silanol groups (Si—OH) are substantially deprotonated at a pH above 2, the wall thereby having negative charges. on its surface. A tightly adsorbed, substantially stagnant layer of cations from a fluid contained in the passage will localize adjacent the negatively charged wall so as to partially neutralize the negative charge on the wall. The remaining negative charge on the wall. is neutralized by excess cations, which remain in the fluid in a more diffuse layer of mobile, solvated cations. The electrical potential across the double layer comprising the wall and the cations is known in the art as "zeta potential". In an electric field, cations are attracted to the cathode, and anions are attracted to the anode. In CZE, the cations in the diffuse layer migrate toward the cathode and, since they are solvated, pull solvent molecules along in their migration, creating a flow of solvent. This solvent flow induced by the electric field, is known as electroosmotic flow (EOF). The velocity of the EOF may be calculated according to equations well known in the art. During electrophoresis, molecules are separated by the EOF in relation to their charge and size. Because fluid flow is generally toward the cathode, molecules tend to elute (be released) from the capillary cations first, followed by neutral molecules having substantially no net charge, followed by anions. Neutral molecules tend not be separated from each other. Various factors may affect the velocity of the EOF, and hence also affect molecular separation. Factors affecting EOF velocity and molecular separation include viscosity of the suspending fluid, particularly adjacent the passage wall, a change in the electrical charge of the wall itself, or alterations to the neutralizing charges overlying the wall.

Polyelectrolytes have been previously used for modifying the electrophoretic properties of fused silica capillary passages. Adsorption of a cationic polyelectrolyte to the negatively charged silica surface effectively reverses the surface charge from negative to positive. This charge reversal causes fluid flow to be toward the anode so that anions elute first, followed by neutral molecules, followed lastly by cations. Polyelectrolytes previously used to coat silica surfaces include polyarginine, chitosan, poly (diallyldimethylammonium chloride) (PDADMAC), and polyethylenimine. Prior electrophoretic techniques have employed single layers of polyelectrolyte.

A method for forming multilayers of polyelectrolytes has now been described. Decher, G. and J. Schmitt, J. *Prog. Colloid Polym. Sci.*, 1992, 89, 160; and Decher, G., *Science*, 1997, 277, 1232. However, the advantages of polyelectrolyte multilayers for capillary electrophoresis have not been recognized before the present invention.

SUMMARY OF THE INVENTION

With the foregoing in mind, the present invention advantageously provides a capillary tube having a multilayer comprising a polyelectrolyte and positioned for analytical separations of molecules.

It is an object of the invention to provide increased electrophoretic efficiency, and substantially equal efficiency at pH of about 4 and about 6.

It is a further object of the invention to provide substantially reproducible electroosmotic mobility among capillaries manufactured using the same procedure.

It is yet another object of the invention to provide a capillary coated with a polyelectrolyte multilayer which may be used for many analytical cycles while yielding substantially reproducible results.

It is a further object of the invention to provide a coated capillary which substantially reduces irreversible adsorption of large polyions such as proteins to the passage wall.

It is an additional object of the invention to provide a coated capillary which is easily manufactured.

It is also an object of the invention to provide a coating for electrophoretic separations which also functions as a partition medium allowing separation of neutral and/or hydrophobic analytes.

It is still another object of the invention to provide a capillary zone electrophoresis system which requires no pre-analysis equilibration, so that a relatively stable electroosmotic flow is obtained substantially more rapidly.

Accordingly, the capillary tube comprises a generally cylindrical void space, or passage, having a lengthwise dimension and a cross section dimension of from about five micrometers to about one hundred micrometers. The multilayer comprising a plurality of polyelectrolyte layers is positioned within the cylindrical void adjacent the walls. The capillary tube may preferably comprise a plurality of layers of a cationic polyelectrolyte and an anionic polyelectrolyte.

An embodiment of the invention includes a plate having a multilayer for analytical separation of macromolecules. The plate comprises a passage substantially defined by passage walls, and a multilayer positioned within the passage adjacent the walls, the multilayer comprising a plurality of polyelectrolyte layers. The passage may preferably be positioned within a capillary tube or within a plate. In addition, the plate may comprise a plurality of passages. The passage preferably comprises walls of fused silica.

In yet another embodiment of the invention, the passage coated with the polyelectrolyte multilayer may further comprise particles coated with polyelectrolyte multilayers. The particles may preferably comprise non-porous silica in approximate sizes from about 1–5 $\mu$m, but may also comprise other suitable materials. Presence of these multilayer coated particles improves separation of neutral molecules by increasing transport of molecular species from the fluid flow into the multilayer. Multilayer coated particles may be included in any of the other embodiments of the present invention, for example in a capillary, or a plate. In addition, the coated particles may also be included in an apparatus embodiment of the invention.

The present invention also includes an apparatus for electrophoretic separation of macromolecules. The apparatus comprises a power supply having a positive electrode and a negative electrode for generating an electric field; a multilayer positioned substantially in a passage formed by passage walls, the passage having a first end electrically connected to the positive electrode and a second end electrically connected to the negative electrode to thereby generate an electric field through the passage, and wherein the multilayer comprises a plurality of polyelectrolyte layers; and a sensor positioned adjacent the passage for sensing macromolecules.

The invention further includes a method for analytical separation of macromolecules. The method comprises the step of forming a passage defined by passage walls. A second step in the method includes positioning a multilayer substantially within the passage adjoining the walls, wherein the multilayer comprises a plurality of polyelectrolyte layers. A third step includes positioning a sample containing macromolecules substantially within the passage. A fourth step includes generating a flow of a predetermined fluid through the passage to thereby substantially separate macromolecules from the sample responsive to an interaction with the multilayer. The flow of fluid may preferably be generated by passing an electric field through the passage, also known as electrophoresis, or by applying pressure to thereby generate the fluid flow.

BRIEF DESCRIPTION OF THE DRAWINGS

Some of the features, advantages, and benefits of the present invention having been stated, others will become apparent as the description proceeds when taken in conjunction with the accompanying drawings in which.

DETAILED DESCRIPTION OF THE PREFERRED EMBODIMENT

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Like numbers refer to like elements throughout, and prime notation when used indicates similar elements in alternative embodiments.

Figure 1:
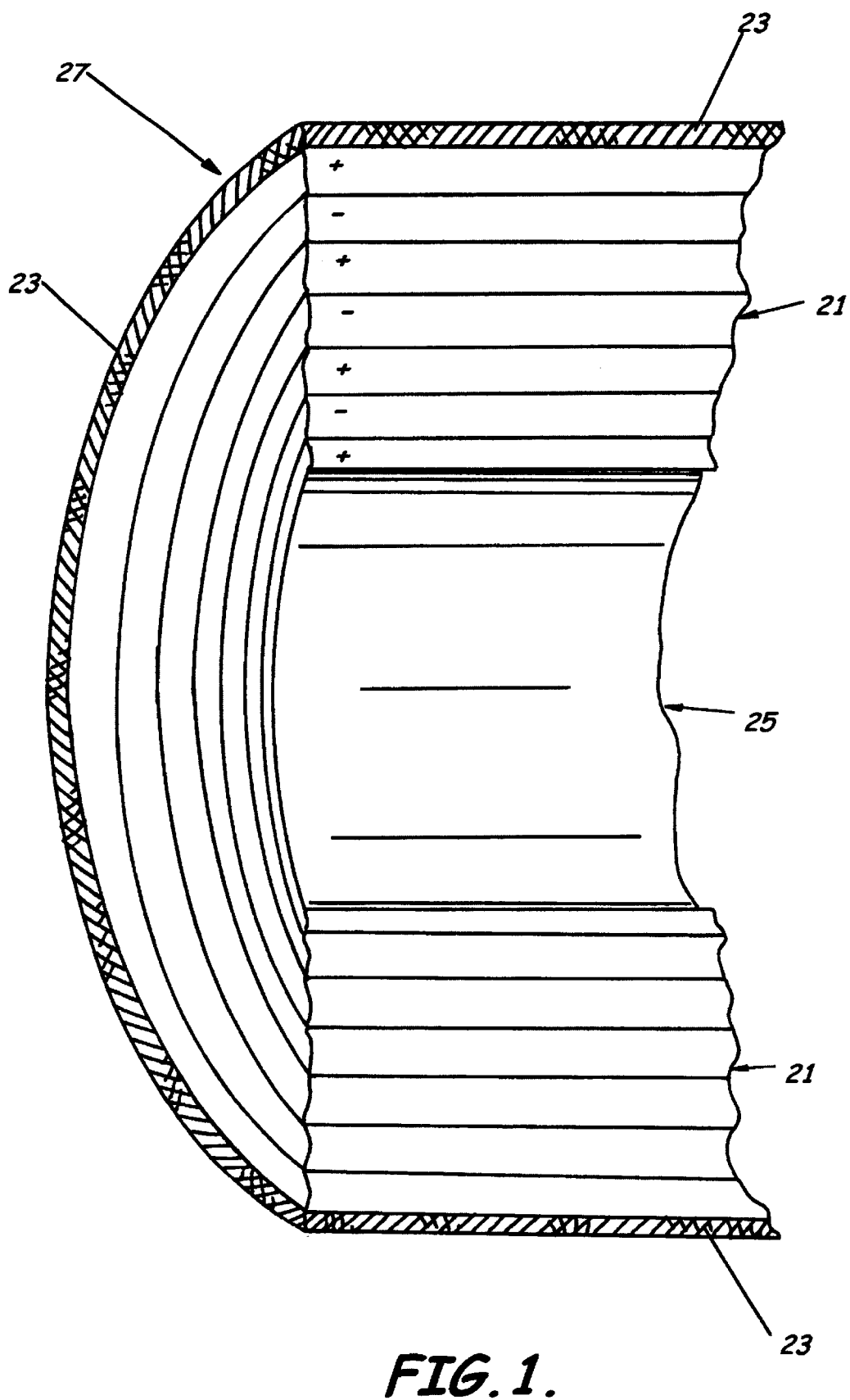
FIG. 1 is a schematic diagram of a capillary tube having a passage wall coated with a polyelectrolyte multilayer according to an embodiment of the present invention.

As illustrated in FIG. 1, the invention discloses an apparatus and method for capillary zone electrophoresis. The invention includes a polyelectrolyte multilayer 21 positioned adjacent the walls 23 of the passage 25, preferably positioned in a capillary tube or a microchannel plate. Those skilled in the art will know that a microchannel plate includes one or more very small passages extending through and enclosed within the plate so as to be a substantial equivalent of the passage of a capillary tube. The multilayer 21 positioned within the passage 25 provides various advantages in analytical molecular separations, and particularly in analytical molecular separations by electrophoresis.

A preferred embodiment of the invention includes a capillary tube 27 having a passage 25 defined by passage walls 23 comprising fused silica. The capillary 27 includes a multilayer 21 positioned within the passage 25 adjacent the walls 23, the multilayer comprising a plurality of polyelectrolytes forming layers, as shown schematically in FIG. 1. Those skilled in the art will readily recognize that a polyelectrolyte is generally a polymer, and particularly an organic polymer, having a permanent or pH-dependent charge. In addition, the skilled artisan will understand that a polyelectrolyte layer pair includes two alternating polyelectrolytes of complementary charge, positive and negative as shown in FIG. 1, coupled by the interaction of those charges, the coupled pair of polyelectrolytes forming one layer pair of the multilayer.

Preferred polyelectrolytes in the present invention include poly(diallyldimethylammonium chloride) (PDADMAC), and poly(styrene sulfonate), sodium salt (PSS). The capillary tube 27 having the multilayer 21 is preferably employed for separating macromolecules by electrophoresis. Those skilled in the art will additionally understand that the term "macromolecule" as used herein is intended to generally include any complex molecule, and particularly those having biological origin and/or biological importance, such as nucleic acids, polypeptides, proteins, enzymes, antigenic molecules, antibodies, polymers, drug molecules, and other natural and synthetic molecules.

In the capillary tube 27, the passage 25 preferably comprises a substantially cylindrical void space having a diameter of from about five micrometers to about one hundred micrometers. The capillary tube 27 includes a first end, a second end, and a lengthwise dimension extending therebetween, wherein the passage 25 extends along the lengthwise dimension from a first opening positioned at the first end to a second opening positioned at the second end.

The multilayer 21 positioned within the capillary 27 preferably further comprises a plurality of layers of an organic cationic polyelectrolyte. In another embodiment the organic polyelectrolyte preferably comprises a plurality of layers of an organic anionic polyelectrolyte. The multilayer 21 may additionally comprise a plurality of organic polyelectrolytes. Additionally, the multilayer 21 in the capillary tube 27 also preferably comprises alternating layers of an organic cationic polyelectrolyte and an organic anionic polyelectrolyte, as shown schematically in FIG. 1. Furthermore, concentration of the polyelectrolyte may vary within the multilayer. In other preferred embodiments of the capillary tube 27, the multilayer 21 may be deposited in the presence of sodium chloride, and may comprise sodium chloride. The multilayer 21 may also preferably comprise a modifier such as an organic solvent, for example ethanol, and may comprise a weak polyelectrolyte. Capillary tubes comprising. a polyelectrolyte multilayer in the present invention are prepared as described in the scientific paper published by Graul, T. W. and J. B. Schlenoff, in *Analytical Chemistry*, 1999, 71, 4007–4013, which is hereby incorporated by reference in its entirety.

Figure 2A:
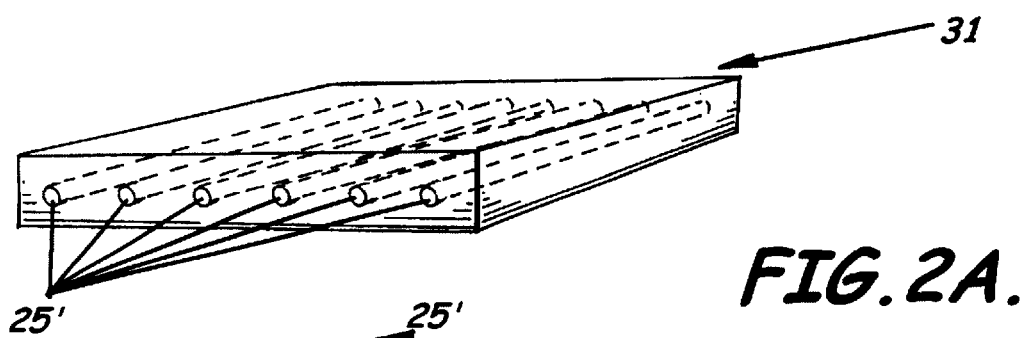
FIG. 2 is a schematic diagram of a microchannel plate.
Figure 2B:
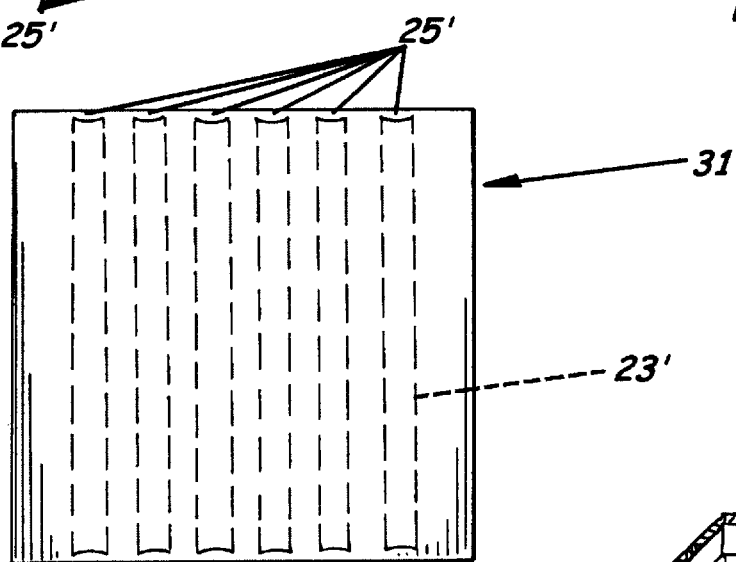
Figure 2C:
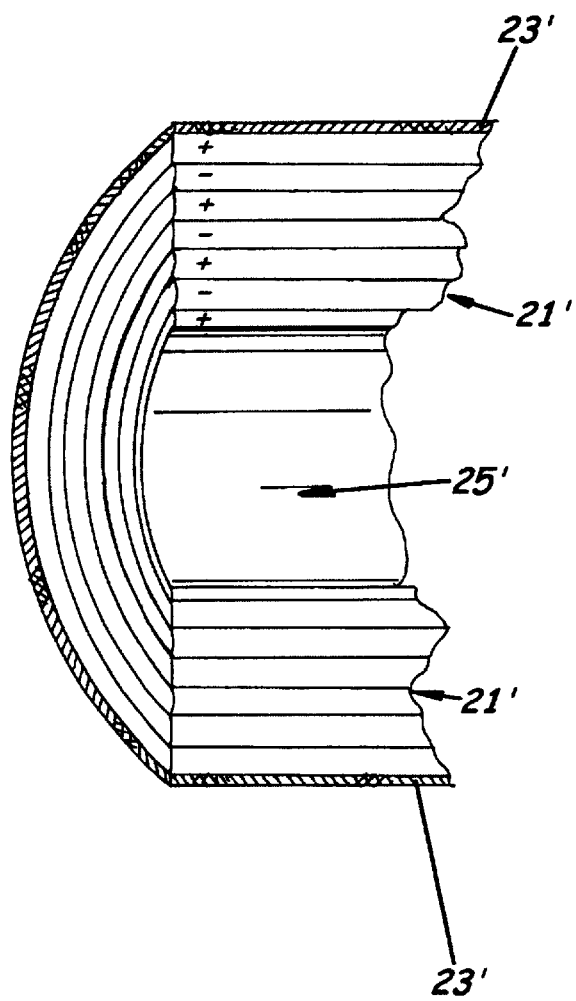

Yet another preferred embodiment of the invention, as shown in FIG. 2, includes a microchannel plate 31 for analytical separation of macromolecules. The plate 31 comprises a passage 25' substantially defined by passage walls. Those skilled in the art will appreciate that, although the passage is shown generally cylindrical in these illustrations, the passage may be formed in many other shapes. In addition, the artisan will know that the plate may be fabricated by various processes, including forming two halves, each half having half of a passage cut into it, the half plates being joined so as to form a complete plate enclosing the passages therein. The microchannel plate passage 25' includes a multilayer 21' positioned within the passage adjacent the walls 23', wherein the multilayer comprises an organic polyelectrolyte. The passage 25' within the plate 31 may comprise a void space having a predetermined lengthwise dimension and a cross section dimension of from about five micrometers to about one hundred micrometers. The passage in the plate may comprise a generally cylindrical void space, such as that of a capillary tube. The passage in the plate also preferably comprises a first end, a second end, the lengthwise dimension extending therebetween, and the passage extending along the lengthwise dimension from a first opening positioned at the first end to a second opening positioned at the second end. In another embodiment, the plate preferably comprises fused silica. Additionally, and as shown in FIGS. 2a and 2b, the plate 31 may further comprise a plurality of passages 25', a particularly useful configuration for running multiple separations simultaneously. However, those skilled in the art will recognize that the passages of the present invention may be formed from any of a variety of materials known to be suitable substrates for such analytical separations, and particularly for electrophoresis.

The multilayer 21, whether positioned within the passage of a capillary or plate, may be formed so that it includes various other components. For example, the multilayer may be deposited in the presence of sodium chloride, and may comprise sodium chloride. The multilayer may also include a modifier, particularly an organic solvent such as ethanol. Inclusion of such components preferably produces a thicker multilayer, or may be used to advantageously provide other useful properties to the multilayer. In addition, the character of the polyelectrolyte within the multilayer 21 may be selected to produce multilayers having different predetermined capabilities. For example, the multilayer may comprise one or more weakly dissociating polyelectrolytes, so as to control the charge of the polyelectrolyte, and thereby the charge of the multilayer, by the pH of the solution.

Figure 3:
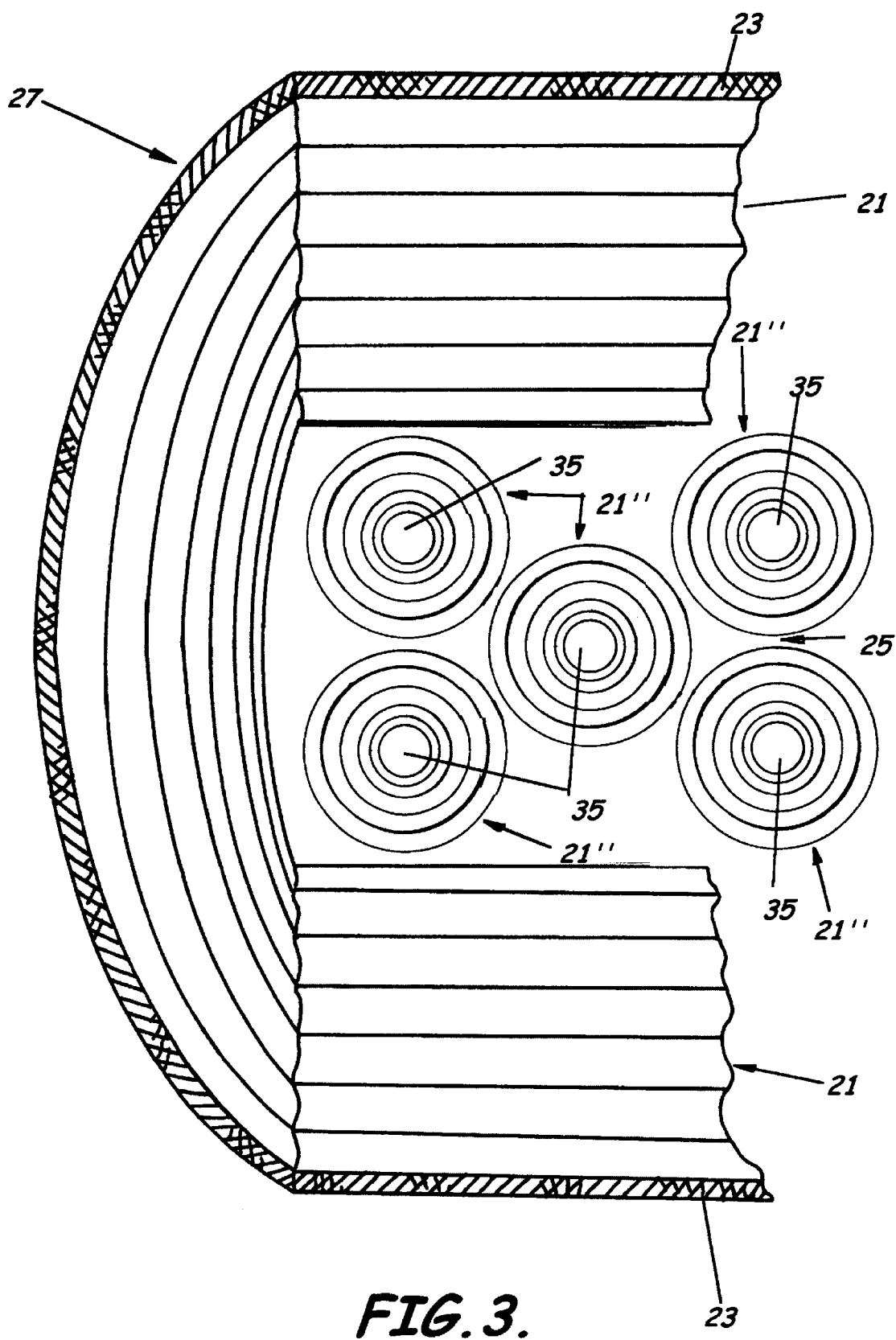
FIG. 3 is a schematic view of the capillary tube passage of FIG. 1 including multilayer coated particles.

In a further embodiment of the invention, shown in FIG. 3, the passage 25 comprising the polyelectrolyte multilayer 21 may be filled with particles 35 ranging in size from about 1–5 $\mu$m, the particles themselves coated with polyelectrolyte multilayers 21". The particles 35, as illustrated schematically in FIG. 3, preferably comprise non-porous silica but may also comprise other suitable materials. Presence of these multilayer coated particles 35 improves separation of neutral molecules by increasing transport of molecular species from the fluid flow into the multilayer. These multilayer coated particles 35 may be included in any of the other embodiments of the present invention, for example in a capillary, or a plate. In addition, the coated particles may also be included in an apparatus 41 embodiment of the invention, as described below.

Figure 4:
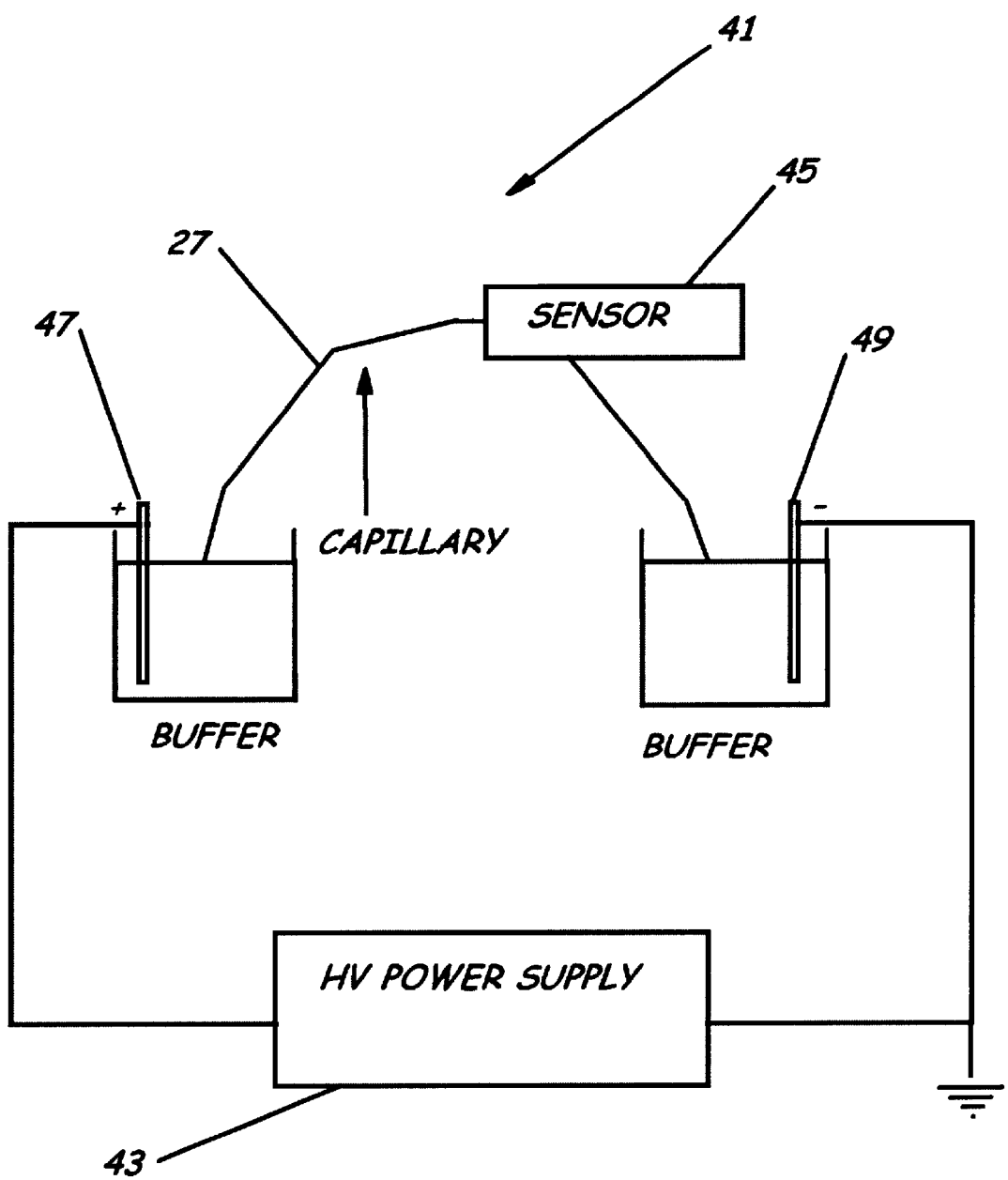
FIG. 4 is a schematic diagram of the apparatus of the present invention.

Another aspect of the invention includes an apparatus 41 for electrophoretic separation of macromolecules. As illustrated in FIG. 4, the apparatus 41 includes a power supply 43, a multilayer positioned in the passage of a capillary tube or plate, and a sensor 45. FIG. 4 illustrates the apparatus 41 embodiment having a capillary 27 comprising the multilayer 21 as illustrated in FIG. 1. The multilayer 21 positioned in the passage 25 comprises an organic polyelectrolyte. The power supply 43 includes a positive electrode 47 and a negative electrode 49 for generating an electric field therebetween. The capillary 27 passage has a first end electrically connected to the positive electrode 47 and a second end electrically connected to the negative electrode 49 to thereby generate an electric field through the capillary 27 passage. The sensor 45 is positioned adjacent the capillary 27 passage for sensing macromolecules, thereby providing information for monitoring the separation.

In the apparatus 41 of FIG. 4, the multilayer is positioned within the passage substantially adjacent the passage walls, and preferably comprises a plurality of organic polyelectrolytes, as shown in FIG. 1. The passage 25 preferably comprises a void space, which may be shaped as a substantially cylindrical passage having a diameter of from about five micrometers to about one hundred micrometers. In a preferred embodiment of the apparatus, as shown in FIG. 4, a capillary tube 27 comprises the passage 25. Alternatively in the apparatus 41, a plate 31 may comprise a single passage, and preferably comprises a plurality of passages 25', as shown in FIG. 2, for running multiple separations simultaneously. As in other embodiments of the invention, in the apparatus 41 the passage walls 23 in either a capillary or plate preferably comprise fused silica. Other aspects of the multilayer included in the apparatus are as described herein for multilayers positioned in a capillary or a plate.

Figure 13:
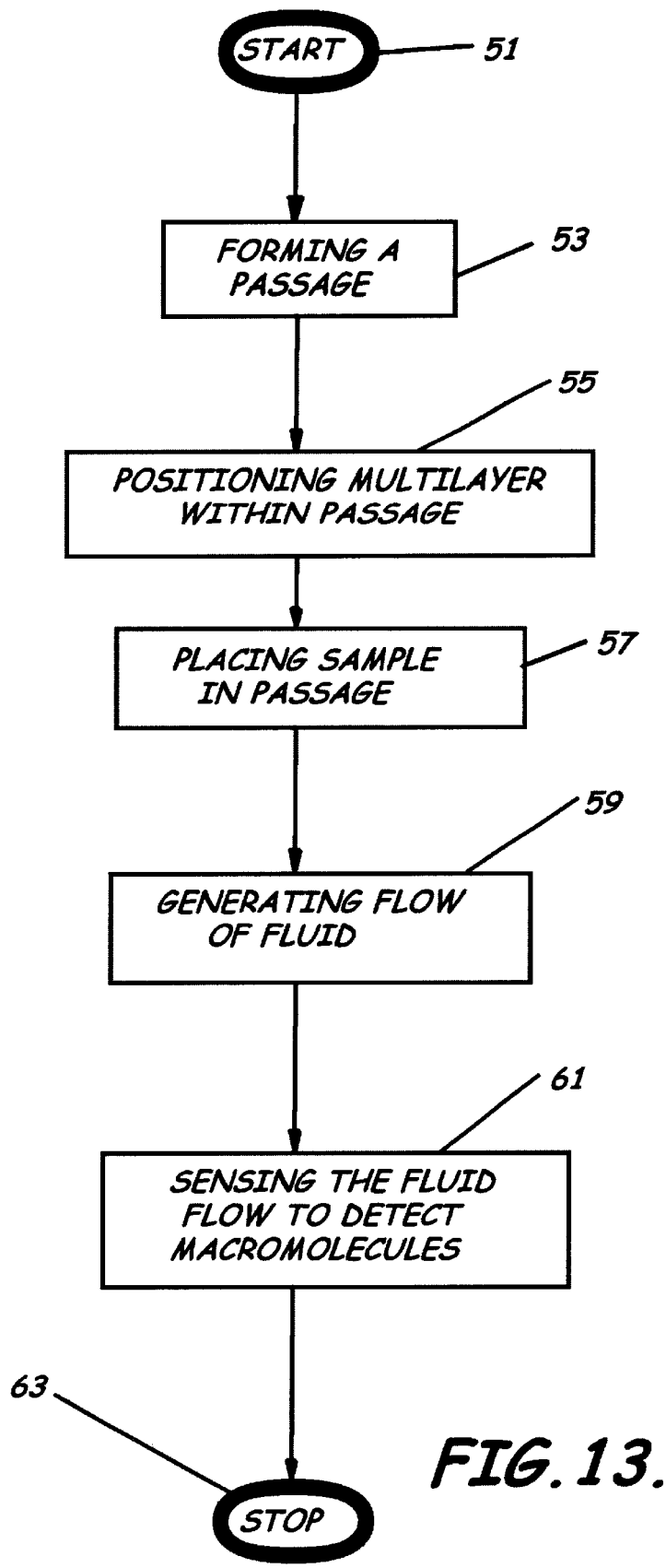
FIG. 13 is a flow chart illustrating the method of the present invention.

A method aspect of the present invention is illustrated in the flow diagram shown in FIG. 13. The method from the start (Block 51) includes the step of forming a passage (Block 53) defined by passage walls. A further step includes positioning a multilayer substantially within the passage (Block 55) and adjoining the walls, wherein the multilayer comprises an organic polyelectrolyte. An additional step includes placing a sample containing macromolecules substantially within the passage (Block 51). A further step is generating a flow of a predetermined fluid (Block 59) through the passage to thereby substantially separate macromolecules from the sample responsive to an interaction with the multilayer. Preferably, in the generating step the fluid is substantially electrically conductive and the flow is generated by applying an electric field through the passage, a process known in the art as electrophoresis. In another preferred embodiment of the method, the flow is generated by applying fluid pressure through the passage, the macromolecules carried by the flow being separated responsive to an interaction with the multilayer. Those skilled in the art will realize that fluid pressure may be generated by applying a compression force or a vacuum force to the fluid.

An additional preferred embodiment of the method further comprises the step of sensing the fluid flow (Block 61) to thereby substantially sense separated macromolecules, whereafter the method stops (Block 63). The step of sensing may be performed by any one of several methods known in the art, for example, absorbance, laser-induced fluorescence, refractive index conductivity, electrochemical detection, and mass spectrometry.

EXPERIMENTAL EXAMPLES

Experimental examples are set forth below in some detail to further illustrate the various features and advantages of the present invention, and as an aid to those skilled in the art in understanding the invention.

General procedures

In general, the materials and methods in the experimental examples are as set forth below and as described by Graul, T. W. and J. B. Schlenoff, in *Analytical Chemistry*, 1999, 71, 4007–4013.

Poly(diallyldimethylammonium chloride), PDADMAC (Aldrich, $M_w$=250,000–400,000, $M_w/M_n$=2.9) and poly (styrene sulfonate), sodium salt, PSS (Scientific Polymer Products, $M_w$=6×10$^6$) were purified by extensive dialysis against distilled water using 12–14,000 molecular-weight-cutoff dialysis tubing (Allied-Fisher Scientific). Basic proteins—Chymotrypsinogen A (Type II from Bovine Pancreas), Ribonuclease A (Type XII-A from Bovine Pancreas), Cytochrome C (from Bovine Heart), and Lysozyme (Grade I from Chicken Egg White) were purchased from Sigma-Aldrich (St. Louis, Mo.) and used as received. Protein sample concentrations before injection were either 0.30 or 0.60 mg mL$^{-1}$. All other chemicals were used as received from Allied-Fisher.

Separations were performed on a Beckman P/ACE System 2100 Capillary Electrophoresis unit (Palo Alto, Calif.) with UV detection. Fused silica capillary with 50 $\mu$m I.D., 360 $\mu$m O.D., and polyimide outer coating was purchased from Polymicro Technologies (Phoenix, Ariz.).

Multilayer coatings were deposited in the capillary tube using the rinse function (rate of 250 cm min$^{-1}$ linear velocity, 5 $\mu$L min$^{-1}$ volume flow rate) on the Beckman CE system. Polymer deposition solutions contained 10 mM polymer, and varying NaCl concentration (polymer concentrations are based on the repeat unit). The capillary was first conditioned by a 30 min rinse of 1 M NaOH. Then water was flushed through the capillary for 3 min. The first monolayer of polymer (PDADMAC) was deposited by rinsing the polymer solution through the capillary for 20 min followed by a 5 min water rinse. All other polymer depositions were done with 5 min rinses followed by 5 min water rinses.

Multilayer coatings used for the protein separations and reproducibility studies comprised six and a half layered pairs (a layered pair generally comprises a layer of a cationic polyelectrolyte and a layer of anionic polyelectrolyte, also termed a "bilayer" in other studies), where the first 3.5 layer pairs were deposited with no salt present and the last three were deposited with 0.5 M NaCl present.

Nonporous silica particles of about 4.5 $\mu$m diameter were coated with polymer by the following method. The particles were suspended in a solution containing 10 mM polymer and 100 mM NaCl. The particles were settled out of suspension with the aid of a centrifuge. The polymer solution was decanted and deionized water was added. The particles were resuspended in the water for several minutes to rinse off any excess polymer. The particles were then centrifuged once again and the water removed. Using this procedure, alternating layers of poly (diallyldimethylammonium chloride) and poly (styrene sulfonate) were deposited onto the silica particles until 20 layers had been deposited. The outer layer comprised poly (styrene sulfonate), giving the particles a negative surface charge.

Particles coated with polyelectrolyte multilayers were suspended in water and pumped under pressure into fused silica capillaries with a sol gel frit at the outlet. The particles accumulated into a packed bed at the end of the capillary. Once the bed formed the particles adhered to each other. The bed was stable, and no secondary retaining frit was used.

The running electrolyte for electrophoresis experiments was phosphate buffer at various concentrations and from about pH 4.0 to 8.0. Electrolyte solutions were made by adding 20 mM solutions of phosphoric acid to 20 mM phosphate salt solutions until the proper pH was achieved. The capillary length was 37 cm, length to detector 30 cm, and the applied voltage was generally 15 kV. UV detection was performed at 254 or 214 nm. Injection of the sample was performed electrokinetically at about 5 kV for 5 sec, ca. 5 nL volume.

Acetone was used as a neutral electroosmotic flow marker, and 2-phenoxypropionic acid (2-PPA) and lidocaine as negative and positive markers, respectively. Standard deviation values are reported as ±1 $\sigma$. Electroosmotic mobility ($\mu_{eo}$) is used here to quantify the electroosmotic flow (EOF) and is given as the velocity of solvent flow per unit electric field strength ($cm^2\ V^{-1}\ s^{-1}$).

Example 1

Advantage of Multilayer over Single Layer

Separation of some representative basic proteins was performed using a capillary having a single layer of polyelectrolyte adsorbed and compared to the separation obtained by using a capillary coated with a multilayer comprising six and a half layer pairs of alternating PDADMAC/PSS layers. Materials and methods were as described, except that for this example electrophoresis was carried out at pH 4.0 in both types of layers. The single layer PDADMAC was deposited from 10 mM polymer solution in $3 \times 10^{-3}$ M NaOH. The multilayer was prepared as described above.

Figure 5:
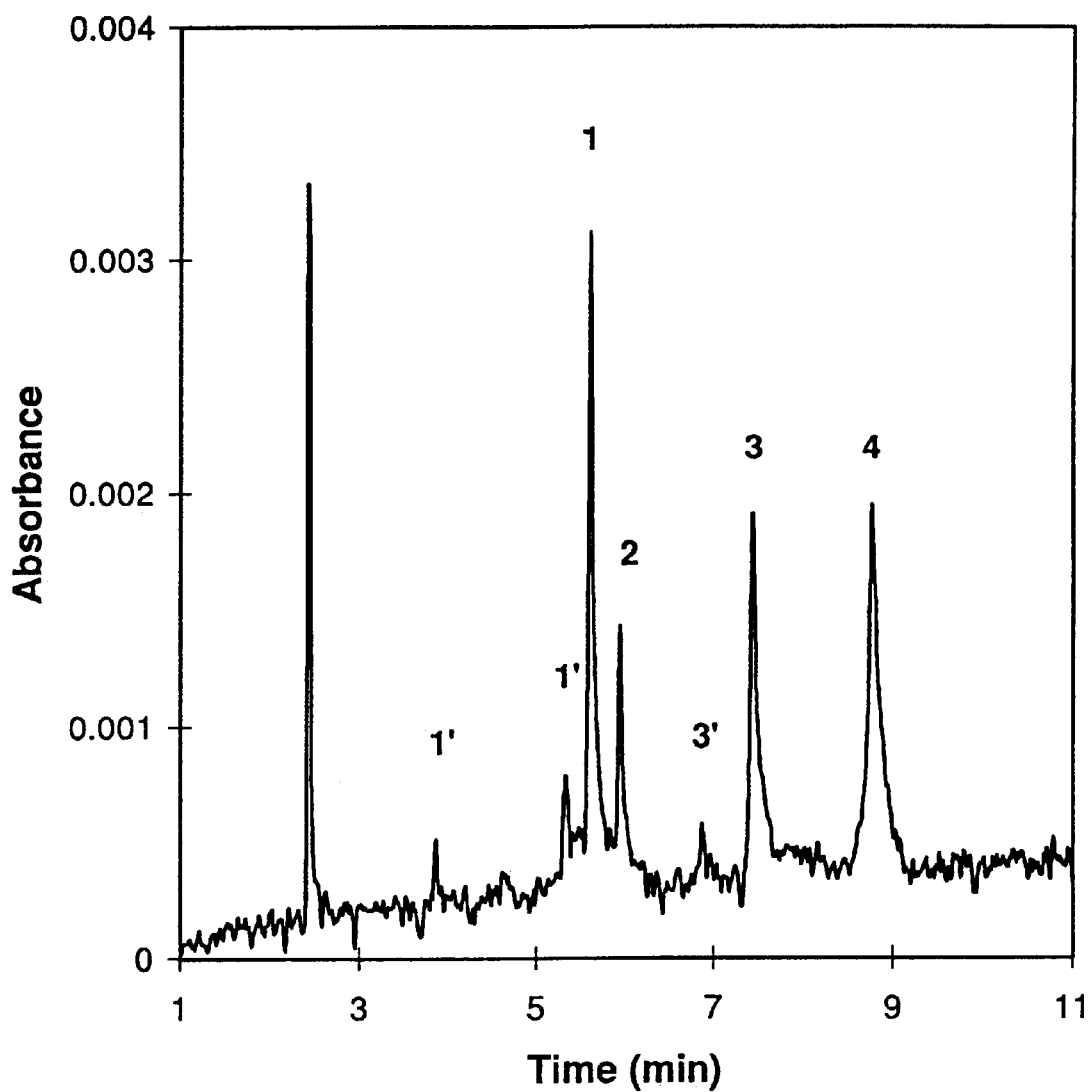
FIG. 5 shows electrophoretic separation of several proteins using a single layer of polyelectrolyte (PDADMAC) at about pH 4, as described in Example 1.
Figure 6:
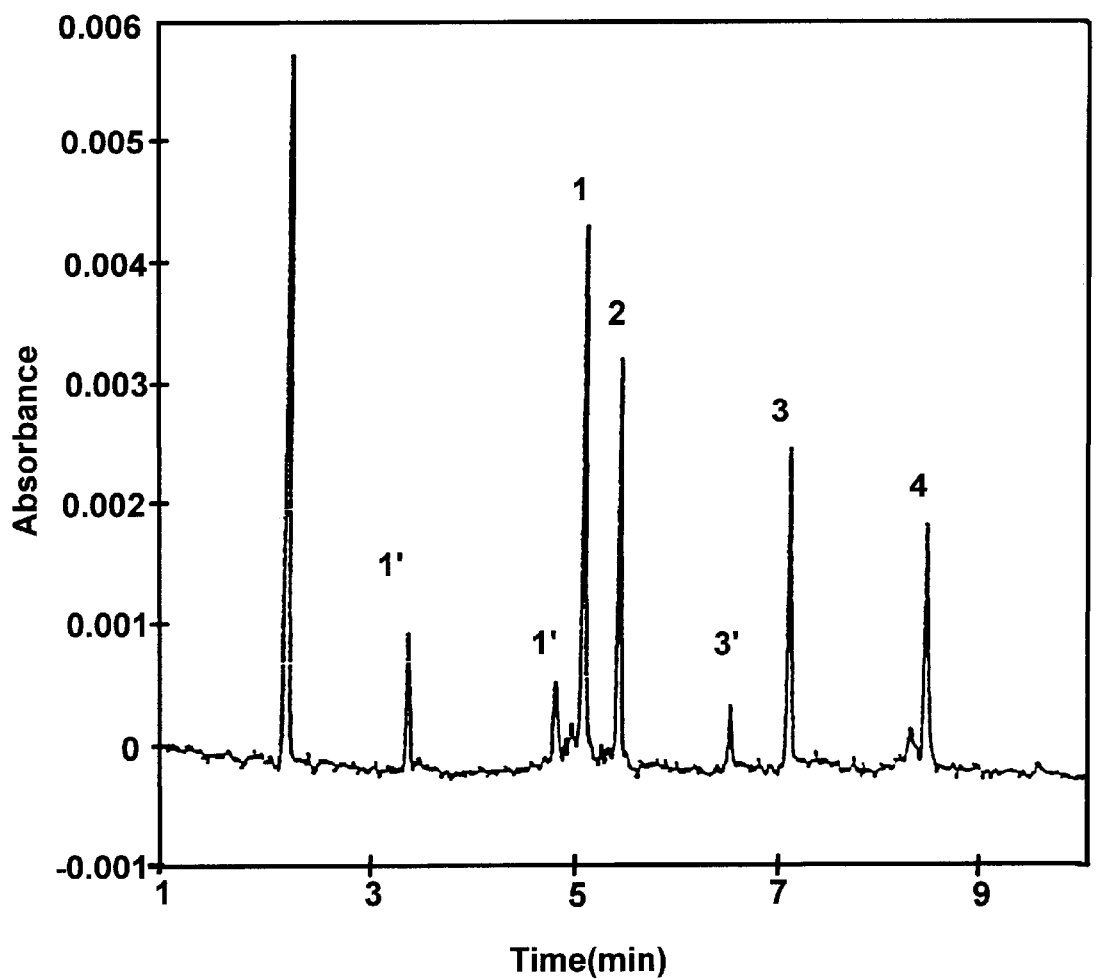
FIG. 6 shows electrophoretic separation of several proteins using a multilayer of polyelectrolytes at about pH 4, as described in Example 1.

FIGS. 5 and 6 illustrate the single layer and multilayer separations, respectively. The first peak in each figure (unlabeled peak) represents 2-phenoxypropionic acid, which was used as a negative marker. The labeled peaks are as follows: 1) $\alpha$-chymotrypsinogen A; 2) ribonuclease; 3) cytochrome C; and 4) lysozyme. Peaks labeled with prime numbers represent impurities or degradation products. Comparing the results depicted in FIGS. 5 and 6, it can be noted that the elution order did not change, and that peak shape is much more symmetrical and narrow for the separation on the multilayer, indicating greater separation efficiency.

A single adsorbed layer of positive polyelectrolyte proved reasonably effective in promoting reversed flow CZE separations of basic proteins, as shown in FIG. 5. However, for separations at pH 6, the single layer column had to be "refreshed" by rinsing with polyelectrolyte in between runs. In addition, some tailing of the peaks was still observed even after rinsing.

Advantageously, capillaries coated with multilayers proved particularly effective in separating the proteins. FIG. 6 shows an electropherogram employing silica coated with 6.5 layer pairs of PDADMAC/PSS. Elution order and migration times are comparable to the results of the single layer PDADMAC column shown in FIG. 5, however, the resolution has improved. In contrast, capillary zone electrophoresis failed to separate the molecules when performed in bare, uncoated capillaries due to irreversible adsorption of the analyte proteins to the passage wall.

Example 2

Separation at Near Physiological pH

Separation was performed using a capillary having a single layer of polyelectrolyte adsorbed and compared to the separation obtained by using a capillary coated with a multilayer comprising six and a half layer pairs of alternating PDADMAC/PSS layers. Materials and methods were as described, except that for this example electrophoresis was carried out at pH 6.0 in both types of layers. The single layer PDADMAC. was deposited from 10 mM polymer solution in $3 \times 10^{-3}$ M NaOH. The multilayer was prepared as previously described.

Figure 7:
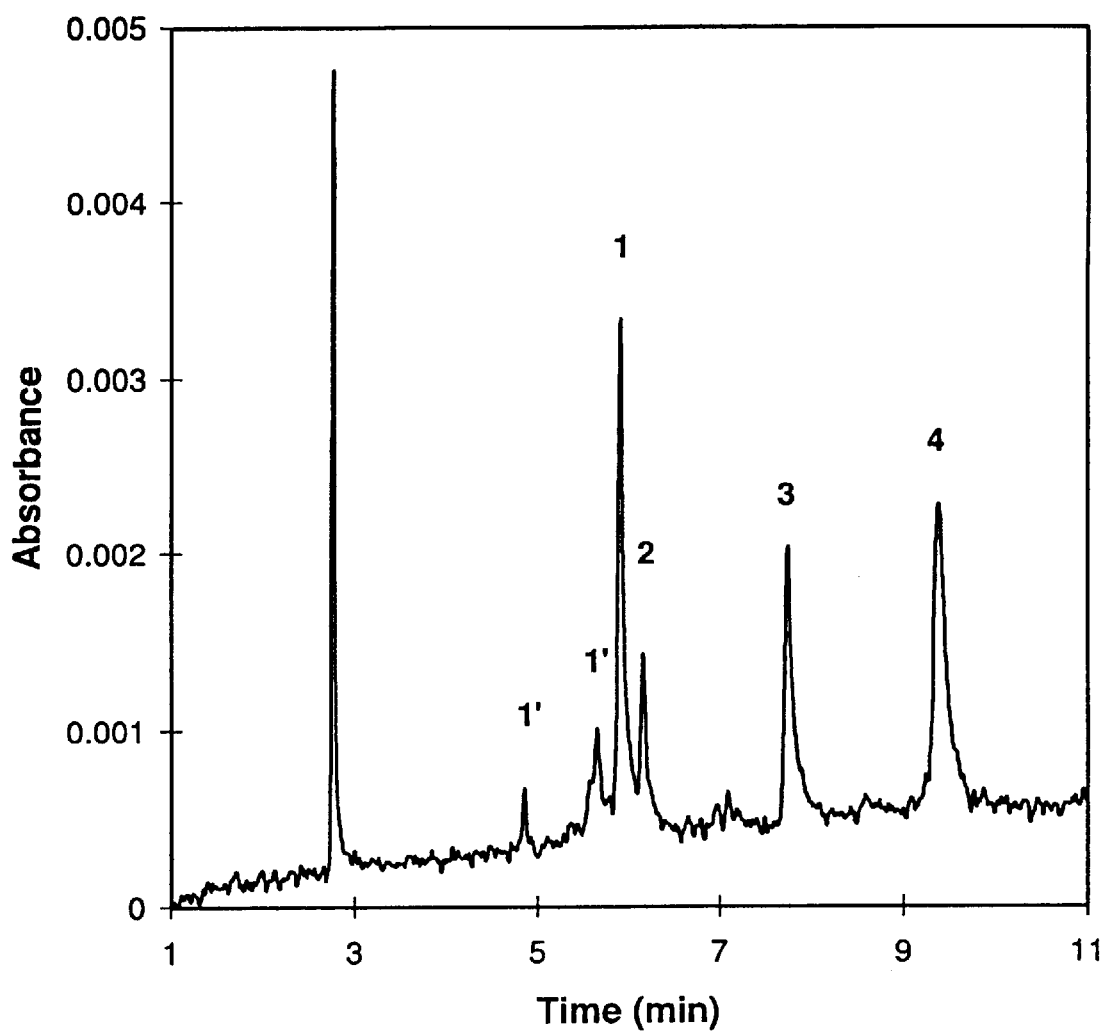
FIG. 7 shows electrophoretic separation of several proteins using a single layer of polyelectrolyte (PDADMAC) at about pH 6, as described in Example 2.
Figure 8:
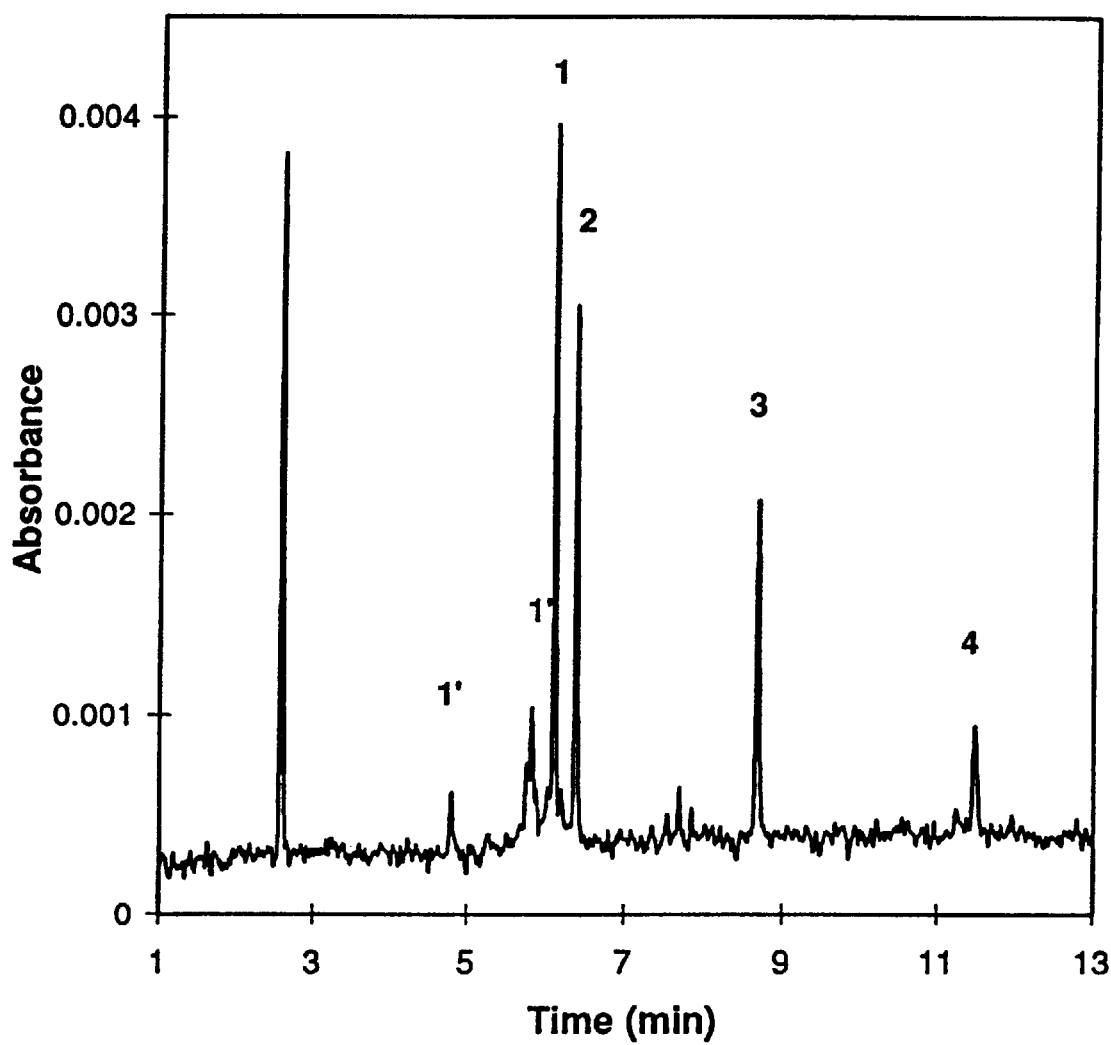
FIG. 8 shows electrophoretic separation of several proteins using a multilayer of polyelectrolytes at about pH 6, as described in Example 2.

FIGS. 7 and 8 illustrate the single layer and multilayer separations, respectively. The first peak in each figure (unlabeled peak) represents 2-phenoxypropionic acid, which was used as a negative marker. The labeled peaks are as follows: 1) $\alpha$-chymotrypsinogen A; 2) ribonuclease; 3) cytochrome C; and 4) lysozyme. Peaks labeled with prime numbers represent impurities or degradation products.

Comparing the results illustrated, it can be noted that the elution order again did not change. The multilayer coating behaved as efficiently at pH 6.0 as at pH 4.0. It is well known that at close to neutral pH separation efficiency is expected to decrease, probably due to adsorption of analytes to uncovered silanol groups on the passage walls. Conversely, proteins tend to degrade at lower pH values, with the resulting degradation. products tending to clutter sensor readings, as noted above. The results illustrated in FIG. 8 for separation on the multilayer at pH 6.0 show that peak height and peak area for impurities are reduced, indicating fewer degradation products present in the sample analyzed. Protein separation and reproducibility of migration times were comparable to results obtained at pH 4.0. Analyte peak shape continues fairly symmetrical and narrow for the separation on the multilayer, whereas the single layer separation indicates less resolution of peaks.

Example 3

Separation of Neutral Molecules

Figure 9:
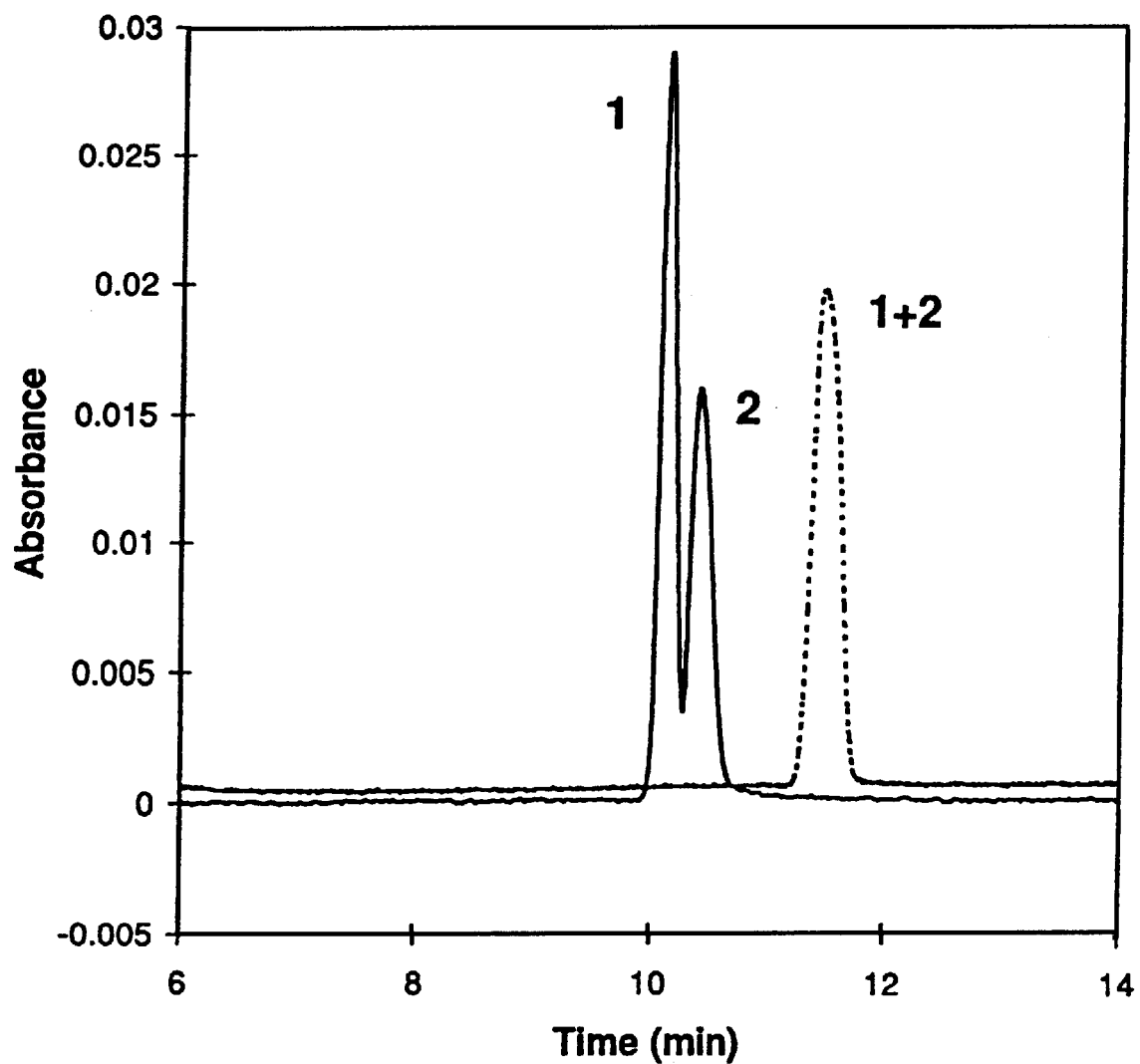
FIG. 9 shows electo-chromatographic separation of two neutral molecules and comparing a single layer of polyelectrolyte with a multilayer, as described in Example 3.

Neutral molecules, which generally tend to migrate together, were used to test separation using a multilayer and compared to an uncoated, bare capillary tube. FIG. 9 illustrates separation results, the solid line indicating separation on a multilayer prepared as described above, and the dashed line indicating the result with the uncoated capillary. Separation conditions were as follows: 37 cm capillary length, with 3.0 cm to the sensor, 50 μm internal diameter, 20 mM phosphate at pH 4.0 as running electrolyte, 5 kV operating voltage, electrokinetic injection of the sample, and detection by the sensor at 254 nm. FIG. 9 shows separation of peaks for 1) acetone, and 2) phenol. The results indicate that, while there was no separation in the bare silica capillary, there was significant separation evident using the multilayer.

Figure 10:
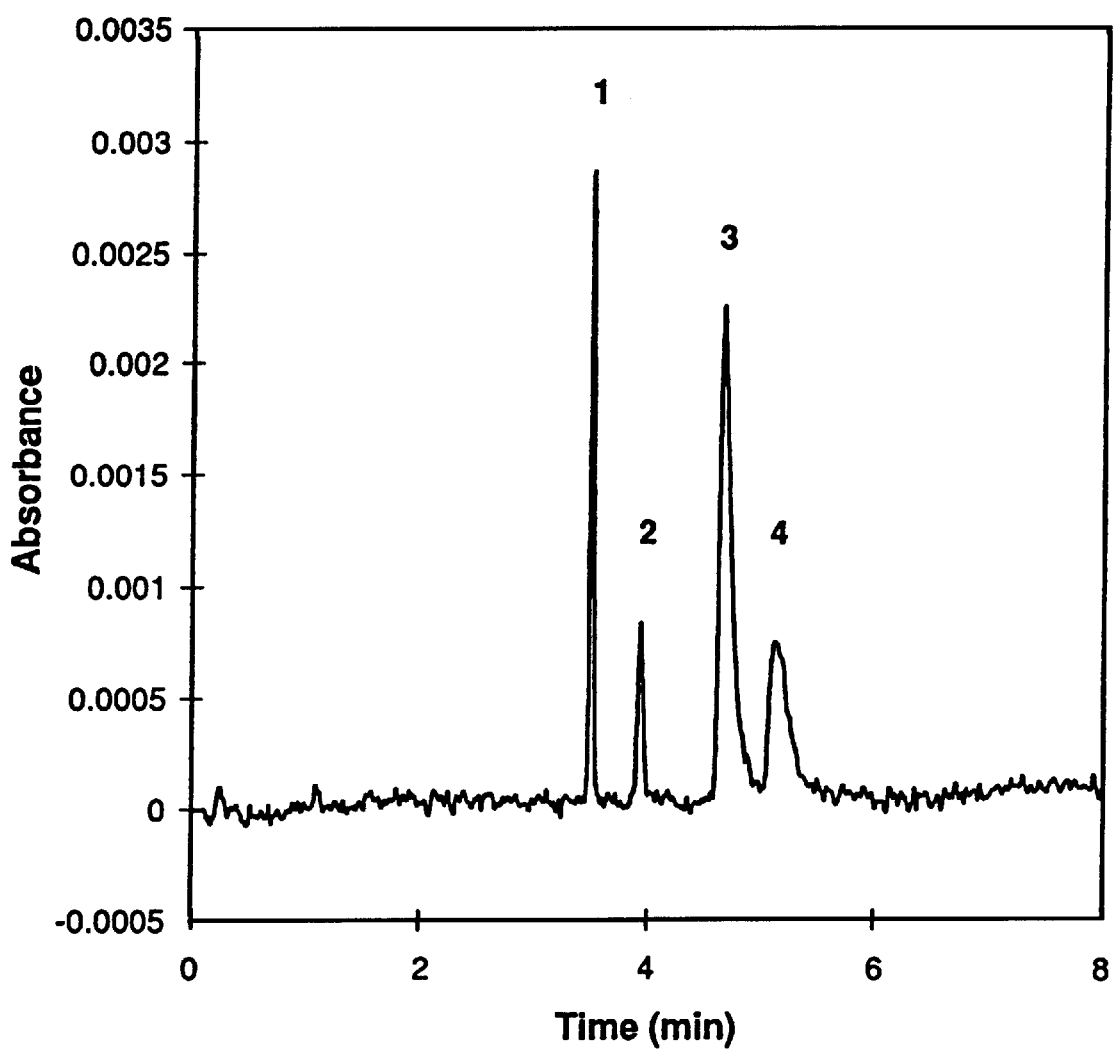
FIG. 10 shows electro-chromatographic separation of four neutral molecules using a multilayer, as described in Example 3.

FIG. 10 illustrates separation peaks for 1) acetone, 2) fluorobenzene, 3) phenol, and 4) p-cresol on a multilayer deposited as described, with the modification of all layers being deposited in the presence of 0.5 M NaCl and 30% ethanol. Separation conditions were as follows: 37 cm capillary length, with 30 cm to the sensor, 50 μm internal diameter, 20 mM phosphate at pH 4.0 as running electrolyte, 15 kV operating voltage, electrokinetic injection of the sample, and detection by the sensor at 254 nm.

Figure 11:
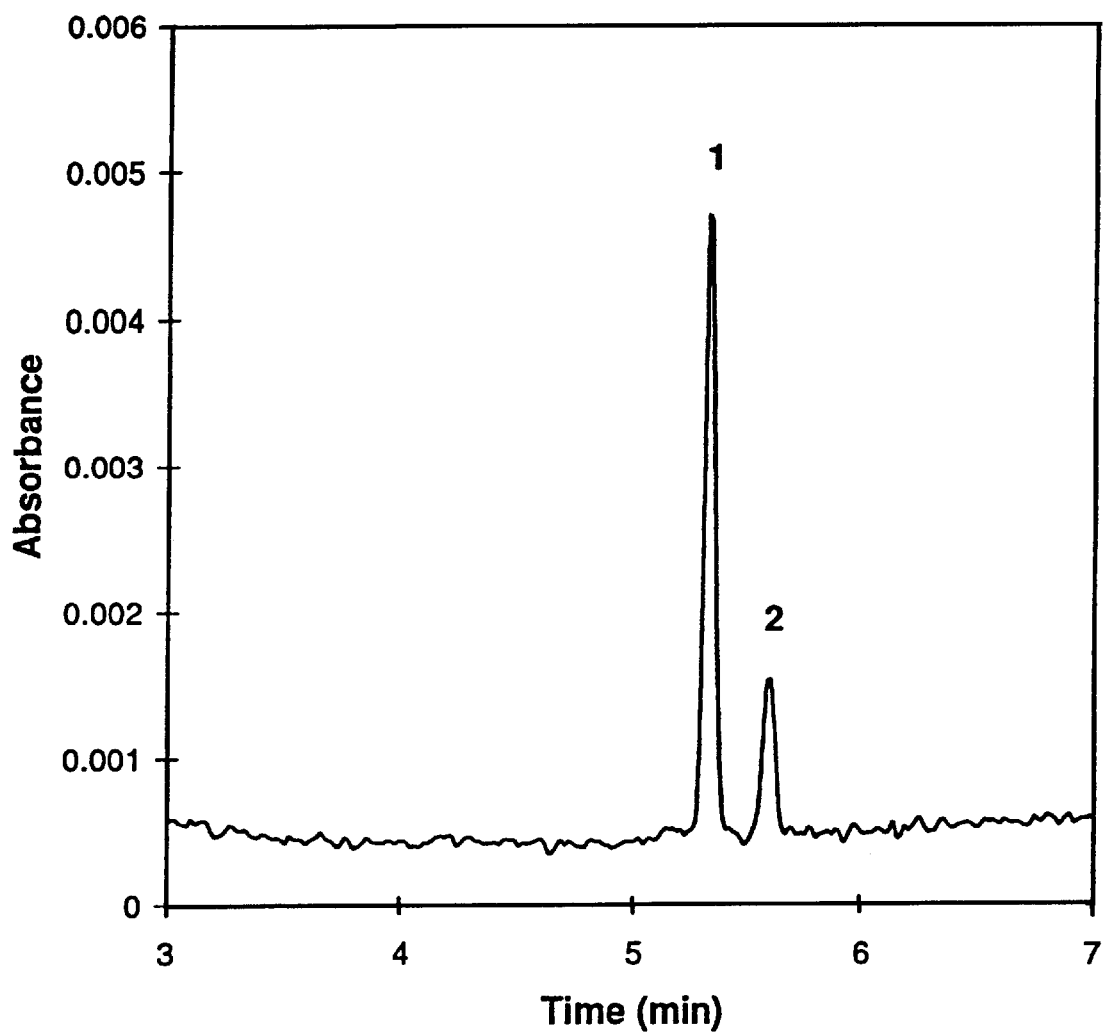
FIG. 11 shows separation of acetone and naphthalene using a multilayer, as described in Example 3.

The multilayer formed in the presence of ethanol did not appear to allow elution of a large neutral solute such as naphthalene. Presence of ethanol during multilayer deposition was shown to produce thicker multilayers, and it is theorized that a large neutral solute would tend to be retained within the multilayer. Therefore, a multilayer formed in the presence of 0.5 M NaCl and 20% acetonitrile was tested for separation and elution of naphthalene. Acetonitrile was used at a lower concentration and, since it is a slightly more polar molecule than ethanol, it was expected to form a thinner multilayer, therefore having a smaller tendency to retain large neutral molecules. FIG. 11 shows separation of peaks of 1) acetone, and 2) naphthalene. Separation conditions included: 80% 20 mM phosphate/20% acetonitrile as the running electrolyte and mobile phase; pH 6.0, 37 cm capillary length with 30 cm to the sensor, 50 μm internal diameter, 15 kV applied voltage, electrokinetic sample injection at 5 kV for 5 seconds, and detection at 254 nm.

Example 4

Separation Using Multilayer Coated Particles

A capillary coated with a polyelectrolyte multilayer was prepared as previously described. Polyelectrolyte multilayer coated particles were prepared also as described above, and packed into the capillary, as illustrated in FIG. 3.

Figure 12:
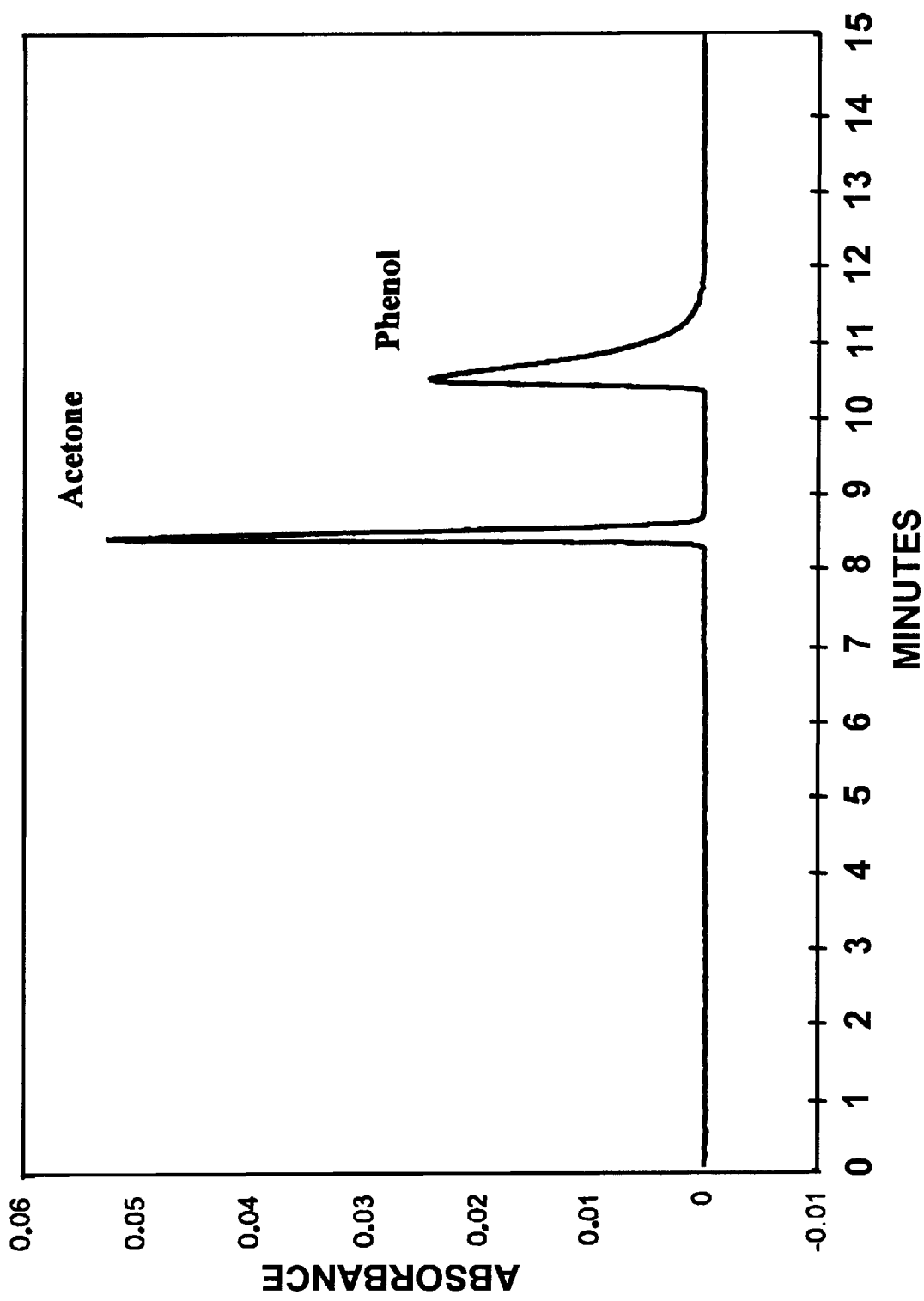
FIG. 12 shows the separation described in Example 4.

Capillary electrochromatography was performed using water as the mobile phase. Acetone was used as the void time marker. Phenol and naphthol were used as test compounds for the separation. Separation conditions were as described in Example 3, above. Illustrative separation results for phenol and acetone are shown in FIG. 12.

In the drawings and specification, there have been disclosed a preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention.

What is claimed is:

1. A capillary tube for analytical separations of macromolecules, said capillary tube comprising:

a passage defined by capillary walls comprising fused silica; and a multilayer positioned within said passage adjacent said walls, wherein said multilayer comprises a plurality of polyelectrolyte layers; and a plurality of particles positioned within said passage, wherein each individual particle comprises a multilayer including a plurality of polyelectrolyte layers.

2. The capillary tube of claim 1, wherein said particles comprise fused silica.

3. The capillary tube of claim 1, wherein said passage comprises a substantially cylindrical void space having a diameter of from about five micrometers to about one hundred micrometers.

4. The capillary tube of claim 1, wherein said capillary tube has a first end, a second end, and a lengthwise dimension extending therebetween, and wherein said passage extends along the lengthwise dimension from a first opening positioned at said first end to a second opening positioned at said second end.

5. The capillary tube of claim 1, wherein said multilayer further comprises a plurality of layers of an organic cationic polyelectrolyte.

6. The capillary tube of claim 1, wherein said multilayer further comprises a plurality of layers of an organic anionic polyelectrolyte.

7. The capillary tube of claim 1, wherein said multilayer further comprises alternating of layers of an organic cationic poly lectrolyte and an organic anionic polyelectrolyte.

8. The capillary tube of claim 1, wherein concentration of said polyelectrolyte varies within the multilayer.

9. The capillary tube of claim 1, wherein said multilayer is deposited in the presence of sodium chloride.

10. The capillary tube of claim 1, wherein said multilayer comprises sodium chloride.

11. The capillary tube of claim 1, wherein said multilayer comprises a modifier selected from organic solvents.

12. The capillary tube of claim 1, wherein said modifier comprises ethanol.

13. The capillary tube of claim 1, wherein said multilayer comprises a weak polyelectrolyte.

* * * * *